United States Patent
Koger et al.

[11] Patent Number: 5,932,035
[45] Date of Patent: Aug. 3, 1999

[54] DRIVE SHAFT FOR ACOUSTIC IMAGING CATHETERS AND FLEXIBLE CATHETERS

[75] Inventors: James D. Koger, Cambridge; Andrew Kapravv, Stoughton, both of Mass.; Kevin R. Heath, Providence, R.I.; Robert J. Crowley, Wayland, Mass.

[73] Assignee: Boston Scientific Corporation, Watertown, Mass.

[21] Appl. No.: 08/781,503

[22] Filed: Jan. 8, 1997

Related U.S. Application Data

[60] Continuation of application No. 08/509,870, Aug. 1, 1995, abandoned, which is a division of application No. 08/144,275, Oct. 29, 1993, Pat. No. 5,437,282.

[51] Int. Cl.⁶ .................................................. C21D 10/00
[52] U.S. Cl. ............................ 148/563; 29/450; 29/451; 604/96; 604/281; 604/282
[58] Field of Search ................ 148/563, 576, 148/402, 902, 908; 604/96, 282; 29/450, 451; 128/662.06, 772

[56] References Cited

U.S. PATENT DOCUMENTS

| | | | |
|---|---|---|---|
| 1,228,439 | 6/1917 | Hotchkiss | 464/7 |
| 4,283,233 | 8/1981 | Goldstein et al. | 148/563 |
| 4,494,833 | 1/1985 | Takamura et al. | 351/41 |
| 4,690,799 | 9/1987 | Yoshida | 420/507 |
| 4,817,613 | 4/1989 | Javaczewski et al. | 128/658 |
| 4,849,032 | 7/1989 | Kawaguchi | 148/11.5 R |
| 4,951,677 | 8/1990 | Crowley et al. | 128/662.06 |
| 5,046,948 | 9/1991 | Miura | 433/21 |
| 5,221,269 | 6/1993 | Miller et al. | 604/281 |
| 5,228,441 | 7/1993 | Lundquist | 128/642 |
| 5,348,017 | 9/1994 | Thornton et al. | 128/662.06 |
| 5,368,049 | 11/1994 | Raman et al. | 128/772 |
| 5,373,619 | 12/1994 | Fleischhacker et al. | 29/451 |

FOREIGN PATENT DOCUMENTS

| | | | |
|---|---|---|---|
| 1/170474 | 7/1989 | Japan . | |
| 1/170475 | 7/1989 | Japan . | |
| 1-242763 | 9/1989 | Japan | 148/563 |
| 3-166347 | 7/1991 | Japan | 148/563 |
| 3/168155 | 7/1991 | Japan . | |
| 4/236967 | 8/1992 | Japan . | |

*Primary Examiner*—Sikyin Ip
*Attorney, Agent, or Firm*—Lyon & Lyon LLP

[57] ABSTRACT

A shaft is shown having inner and outer members in interfering contact along their length, at least one of which comprises a wire, at least a portion of which is superelastic, to achieve substantial mechanical fidelity and resistance to damage. An ultrasound imaging catheter has a hollow catheter shaft, an ultrasound transducer in the shaft, and a drive shaft that rotates the transducer. The shaft comprises at least one metal coil having characteristic elastic deformation under stress in the range of about 3% to 9%, while a restraint means prevents torsional deflection of the coil. A drive shaft having a coil surrounded by a tube, a coil bonded to an inner coaxial cable, and an inner and outer coil that interfere with one another are shown. A superelastic coil is formed by continuously winding a wire about a mandrel, heating a region of the wire to render it superelastic, and after cooling, removing it from the mandrel.

14 Claims, 4 Drawing Sheets

DRIVE SHAFT FOR ACOUSTIC IMAGING CATHETERS AND FLEXIBLE CATHETERS

This is a continuation of application Ser. No. 08/509,870, filed on Aug. 1, 1995, now abandoned, which is a divisional of application Ser. No. 08/144,275, filed Oct. 29, 1993, now issued as U.S. Pat. No. 5,437,282.

BACKGROUND OF THE INVENTION

This invention relates to drive shafts used in acoustic imaging catheters.

Acoustic imaging catheters are used in medicine to visualize the internal conditions of the body, such as the condition of the walls of the vascular system. The imaging catheters comprise a transducer probe attached to the end of a flexible rotating drive shaft. The drive shaft is used to insert the transducer into the body, and to rotate the transducer at high speed to produce a 360 degree image.

One drive shaft that has been employed comprises two cross-wound, multifilar stainless steel interlocking coils, as described in Crowley et al., U.S. Pat. No. 4,951,677, incorporated by reference.

It is important that the drive shaft be flexible enough to pass through tortuous passages in the body. The drive shaft should also have one-to-one rotational fidelity between its proximal and distal ends to avoid image smearing. Acoustic imaging is made more powerful when the drive shaft, and consequently the catheter itself, has a very small outer diameter, enabling it to penetrate into more restrictive regions of the body.

SUMMARY OF THE INVENTION

In acoustic imaging catheters there has been difficulty in achieving true one-to-one fidelity between the rotation of the driver at the proximal end of the catheter, and the rotation of the transducer at the distal end. Lack of such fidelity produces artifacts in the image that impairs its quality and usefulness. To address this problem, attention in the past has been paid to maximizing the torsional rigidity of the flexible drive shaft employed.

We have discovered that lack of fidelity can be addressed in another, highly effective way, by employing a drive coil fabricated at least in part of relatively low modulus of elasticity metal, e.g. having elastic deformation in the range of about 3% to 9%, preferably employing superelastic metal with recoverable deformation in the range of 4% to 7%. We have realized that the relative kink-resistance of a coil of such metal prevents the formation of micro-kinks and other disturbances in the geometry of the drive coil, such that, during rotation, the coil rotates much more smoothly when bent into the curves that occur in the natural ducts of a patient, e.g. the aortic arch. With such a coil we realize that the rotational velocity of the distal tip will match very closely the rotational velocity of the proximal driver.

According to one aspect of the invention, a flexible, rotatable shaft is provided, comprised of inner and outer tubular members in mutually interfering contact along their length, at least one of the tubular members comprising a wire, at least a portion of the wire being exposed to forces tending to produce kinks, the portion being comprised of a superelastic alloy, whereby substantial mechanical fidelity is achieved and resistance to damage improved by virtue of the superelasticity of the portion of the rotatable shaft.

According to another aspect of the invention, an ultrasound imaging catheter is provided, comprising a hollow catheter shaft, an ultrasound transducer located distally from the proximal end of the hollow shaft, and a drive member extending from a proximal drive mechanism, through the hollow shaft to the transducer and being rotatable within the hollow catheter and in rotatable drive relationship with the transducer, the drive member comprising an elongated rotatable shaft comprised of at least one tightly wound coil of metal having characteristic elastic deformation under stress in the range of about 3% to 9% and a restraint means associated with the coil over the length of the coil effective to prevent torsional deflection of the coil. Preferably in this ultrasound imaging catheter, the metal is superelastic.

In another preferred embodiment, a torque transmitting elongated assembly, e.g a torquable catheter, useful for introduction through a duct of the body comprises an elongated rotatable shaft of at least one tightly wound coil of metal. The metal has a characteristic elastic deformation under stress in the range of about 3% to 9%. The assembly also has a restraint means over the length of the coil to prevent torsional deflection of the coil.

In the presently most preferred embodiment, the drive shaft or the torque transmitting assembly comprises inner and outer, closely wound multifilar coils, the coils being wound in opposite directions, each fabricated of superelastic metal, the coils held together in interfering relationship such that they mutually resist unwinding in response to torque or change in torque conditions. Preferably, during manufacture, the inner coil, after fabrication and heat treating to render it superelastic, is wound down on a smaller mandrel with elastic deformation, thus achieving a smaller diameter before insertion into the outer coil, so that upon release it will spring to a larger diameter to achieve at least an original level of interference with the outer coil. In preferred embodiments, the multifilar construction is comprise of between 3 and 10 filaments.

Other embodiments, however, are within the broader aspects of the invention.

A drive coil of superelastic metal is advantageously combined with another elongated device that provides resistance to winding or unwinding of the coil. Among such embodiments is a dual coil assembly, in which only the outer coil is superelastic; because the outer coil is exposed to the greater kink-producing stresses, such a combination offers advantages of the invention, while being easy to assemble. The inner coil, formed e.g. of stainless steel, can be held in its original coiled state during insertion, but when released during assembly, will tend naturally to spring to a larger, interfering diameter with the outer superelastic coil, without need for special steps.

Another preferred embodiment comprises the combination of a closely wound multifilar coil of superelastic metal, about which a thin stretch-resistant sleeve of stiff polymeric material is closely fit, or about which such a tube is heat-shrunk. The resistance to kinking is again achieved by the superelastic coil, while the sleeve resists any tendency for the coil to unwind. As the wall thickness of such a sleeve can be of the order of 0.0002 inch (0.005 mm) the entire assembly can be quite small, capable of accessing very restricted regions of the body. In some embodiments, the coil is expanded into interfering contact with the surrounding sleeve.

In still another preferred embodiment, there is a tightly wound multifilar coil of superelastic metal, through which a co-axial cable is threaded, for communication to and from the distal transducer from the proximal end, the coaxial cable in this case serving as an unwind-resistant member, the coil being bonded along its length to the surrounded coaxial cable.

In another preferred embodiment of the invention, a coil of superelastic material is formed from a running length of wire with latent superelastic properties from a supply. The wire is wound continuously about a mandrel before being heated to stress relieve the wire and render it superelastic. After the coil is formed, it is removed from the mandrel.

In preferred embodiments, winding is performed by a pair of winding points, and in other embodiments the winding is performed by a rotating die. In preferred embodiments, the heating and winding are performed while the length of wire is in an inert gas chamber.

Nitinol coils manufactured in the various ways described above can be joined to or embedded in the walls of thin tubes, or coated to form such tubes, to enhance the compression resistance of thin walled tubular members over a wide range of tube diameters for use in catheters. The provision of such kink resistant catheter walls is another important feature of the present invention.

In various preferred embodiments, the wire of the coil is of circular cross section; in other embodiments the wire is of oval cross section, and in other embodiments the wire is of rectangular cross section. Preferably, the wire of which the coil is comprised is of radial dimension between about 0.012 and 0.001 inch depth.

BRIEF DESCRIPTION OF THE DRAWINGS

FIG. 1 is a schematic diagram showing introduction into the body of an acoustic imaging catheter according to the invention, while

DESCRIPTION OF THE PREFERRED EMBODIMENTS GENERAL STRUCTURE

Figure 1:
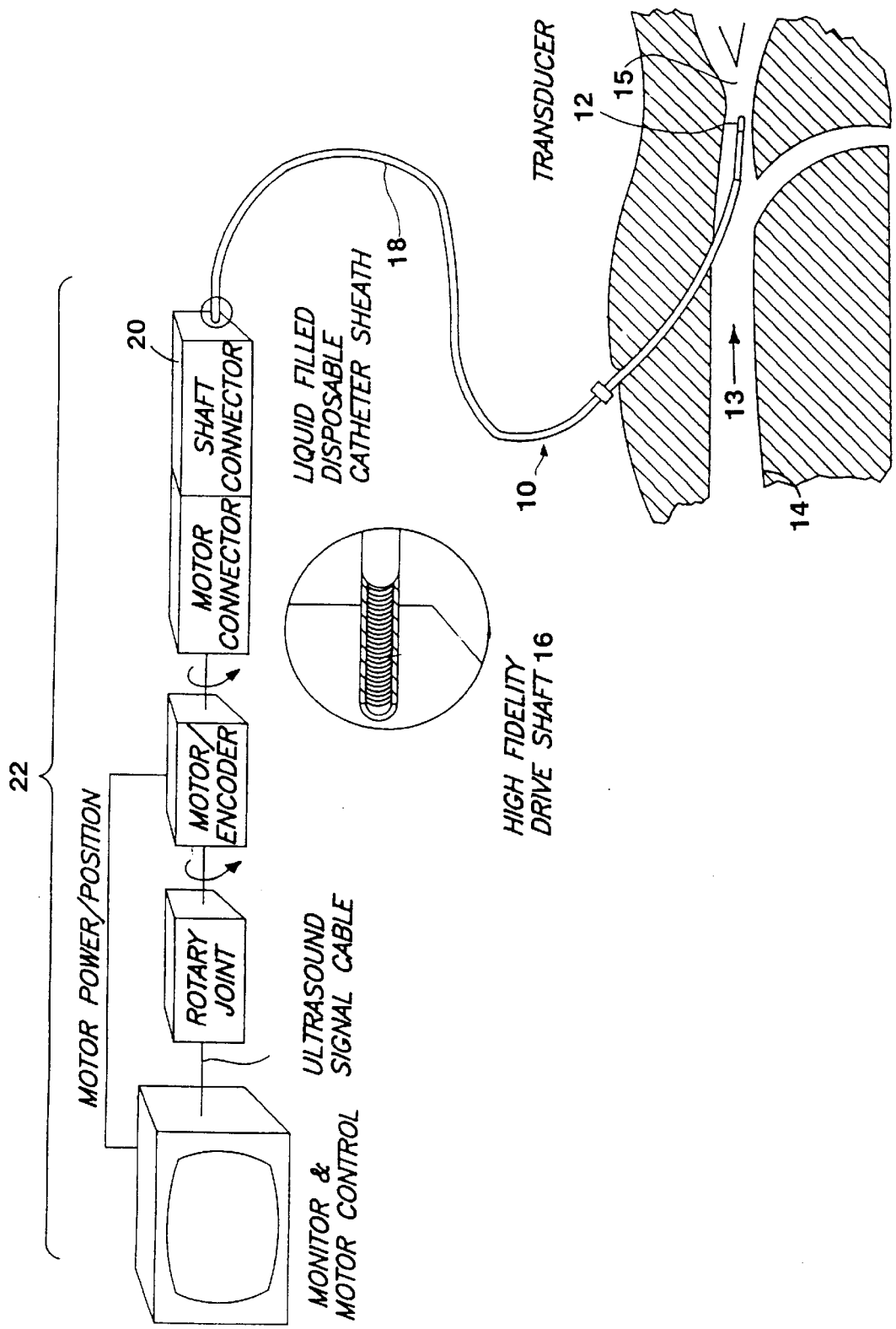
Figure 2:
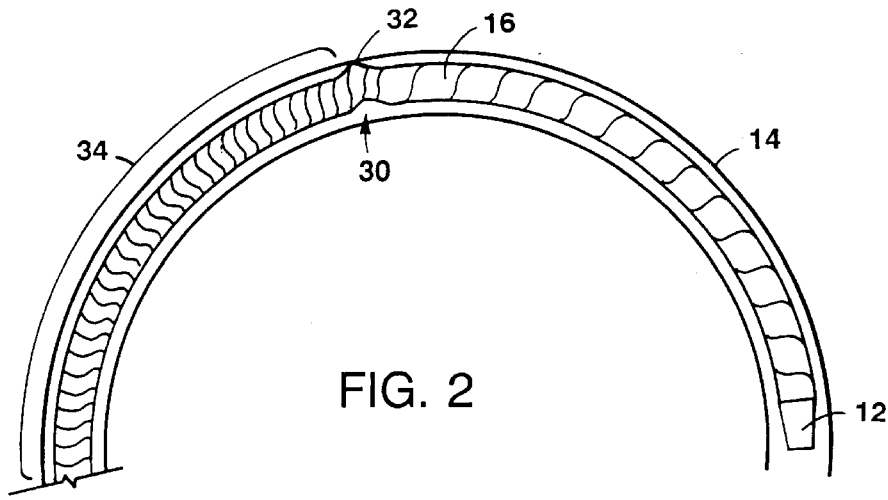
FIG. 2 illustrates severe bending of the catheter as it accesses the heart.

Referring to FIGS. 1 and 2, a micro acoustic imaging catheter 10 images the body with a miniature rotatable transducer 12 in its distal end 13 which is positioned in the body, e.g. in a blood vessel 14 or the heart 15. The transducer is driven by a hollow drive shaft 16 placed within a catheter sheath 18. A coaxial cable inside the drive shaft connects the transducer to a relatively rigid connector 20 joining the catheter to a control system 22. The control system moves the catheter and monitors and displays the returned transducer signal.

In an ultrasound imaging system, the relative position of the ultrasound transducer must be accurately known at all times to avoid image distortion of the return signal at the controller. Since the position information is measured from the proximal end 24 of the drive shaft in the preferred embodiment, it is important to have a one-to-one transmission of motion with complete fidelity, meaning that a rotation of the proximal end of the drive shaft at a constant speed causes the transducer to rotate at a corresponding constant speed.

We have realized that even a high fidelity drive shaft may not have a constant rotation speed at the distal end due to miniature kinks and other permanent small distortions that may arise, for instance due to being coiled on the shelf for a period or subject to mishandling. Blur in the image due to lack of one-to-one fidelity is termed drive shaft artifact.

Structure of the drive shaft

Figure 3:
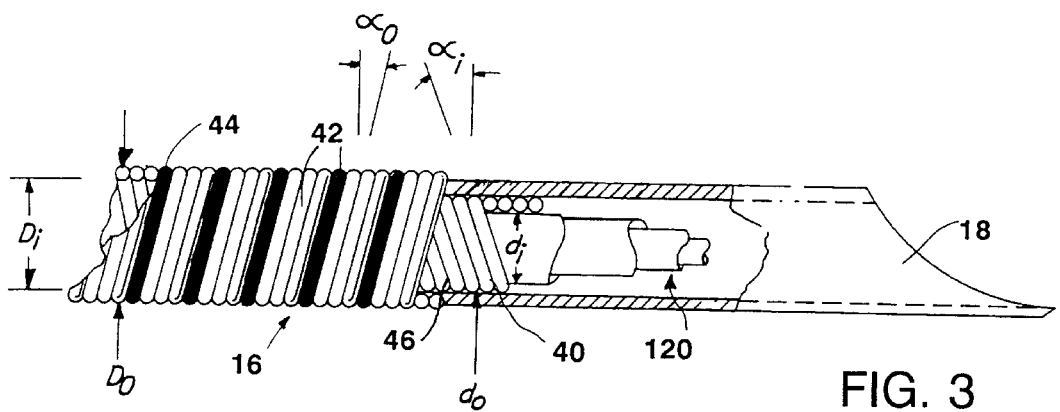
FIG. 3 is a longitudinal, partially cut-away view of the distal end of the catheter.

By forming a drive shaft coil, in at least its critical region, from a metal whose characteristics permit a substantial amount of recoverable strain, e.g. superelastic nitinol material, we realize that these detrimental microkinks can be avoided. Referring to FIG. 3, the drive shaft 16 in one embodiment comprises an inner coil 40 and outer coil 42 of wound nitinol. The outer coil has an outer diameter $d_o$ of 0.03" and an inner diameter $d_i$ of 0.017" and the inner coil has an inner diameter $D_i$ of approximately 0.010" and an outer diameter $D_o$ of 0.015". Each coil is of multifilar construction, having between 3 to 10 filaments, one of which (44) is shown by shading, each made of a wire with a minimum cross-sectional diameter of about 0.002". In other embodiments, the outer diameter of the drive shaft as a whole ranges from about 0.012" to about 0.06", with wire diameters ranging from about 0.002" to about 0.007", respectively.

The coils are closely wound, in counterwound relationship, with an inner pitch angle $\alpha_0$ and $\alpha_1$ where $\alpha_0$ is smaller than $\alpha_1$, e.g., 22.5 and 31 degrees, respectively. The pitch angles are chosen to eliminate space 46 between turns of the wires, and to apply a substantial part of the stress from either tension or compression in the direction along the axis of the wire filaments. The two coils fit together, as described below, so that they interfere with one another when rotated in a given direction, i.e. the outer coil will tend to contract while the inner coil tends to expand, each thereby resisting the radial change of the other. The interference significantly increases torsional stiffness in the rotational direction, resulting in a high fidelity drive shaft.

In this preferred embodiment, each coil in the drive shaft is made of a nitinol alloy, having an ultimate tensile strength of 250,000 to 300,000 psi when drawn. The alloy is available from Furukawa Electric Company located in both Japan and California. After winding, the coils are heat treated to render them superelastic.

Figure 4:
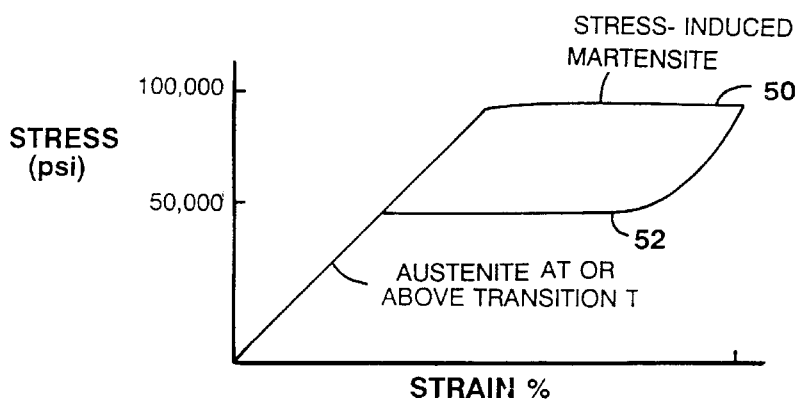
FIG. 4 is a stress-strain curve for superelastic nitinol.

During use, the nitinol alloy exhibits superelastic characteristics under stress, i.e. it undergoes reversible deformation, changing from Austenite to stress-induced Martensite, as shown in FIG. 4. When optimized for superelasticity at body temperature, the alloy has a loading plateau 50 of approximately 100,000 psi, and an unloading plateau 52 of approximately 50,000 psi with a temperature transition ($A_f$) of around 0 to 5 degrees C.

In other embodiments, the wire is a nitinol alloy selected from a wide range comprising from about 40% to 60% nickel with the majority of the balance being titanium. Nitinol alloys having a third element, for example, chromium, vanadium or iron as a third element are generally stiffer and stronger than a pure nickel-titanium alloy. The preferred range for the ultimate tensile strength of the nitinol alloy is from 200,000 to 400,000 psi with the material exhibiting 3% to 9% reversible elastic deformation; a particularly useful material has 275,000 psi tensile strength with 7% elastic deformation. The lower range of elastic deformation (3–4%) is provided by either cold worked, non-superelastic Martensite or Austenite nitinol alloy, or in some cases titanium alloys.

Alloys below the lower limit of elastic deformation (about 3%) though in some cases providing good torsional fidelity do not demonstrate the beneficial properties achieved with the present invention. Alloys with elastic deformation above the upper bound, about 9%, permit detrimental windup in a coil that results in drive shaft artifact.

Coils that are small in diameter (e.g., 0.020" outer diameter or less) are in some cases made of alloys with higher tensile strengths, up to 400,000 psi. A higher tensile strength is achieved by increasing the percentage of nickel in the alloy.

The cross section of the nitinol wire in various embodiments is circular, oval or rectangular, with a radial dimension (diameter in the case of a circular cross section) ranging from 0.001" to 0.012". A circular cross section provides the greatest coil flexibility and largest coil wall thickness, whereas a rectangular cross-section decreases the wall thickness at the expense of some loss of flexibility. A rectangular cross section is appropriate, for instance, when the need for smallness of the drive shaft is the primary constraint and when flexibility is relatively less important, for example, when the drive shaft does not have to bend tightly but the catheter's outer diameter must be 0.020" or smaller. Such wire may be of strip form of thickness about 0.002". The stiffness of the rectangular wire is minimized by decreasing the width of its cross section, i.e. in the direction of becoming square.

An oval cross section is seen to be a useful compromise between these two forms in certain instances, having the advantage of lowering the wall thickness while providing significant flexibility.

Under certain circumstances it is conceived to use triangular cross sections to provide high flexibility in selected regions of the drive shaft. A triangular wire flexes uniformly and provides space between each coil to flex into the other, instead of rolling over one another.

Manufacture of the drive shaft

The drive shaft is manufactured by first winding the selected number of nitinol wire filaments into a coil about a mandrel and securing its free end in tightly wound condition, preferably by means of adhesive, tape or a clamp. The tightly wound coil, while remaining on the mandrel, is then subjected to an annealing temperature of 450 C. for fifteen minutes to render it superelastic.

In another embodiment, heating is progressive, only a small section of wire being heated to 450 C. at any time as it is being continuously wound around a mandrel. The continuous coil coming off the mandrel is then wound on a drum.

If the outer coil of an interfering coil construction is first produced by the process described above, the next step is to wind the inner coil tightly on a mandrel, in a direction opposite to the direction of winding of the outer coil. The inner coil is then heat treated identically to the outer coil and removed from the mandrel. The inner coil is now tightened by sliding it onto a smaller mandrel, securing it at one end, and then either winding, preferably, or stretching the coil, until the coil's inner diameter conforms to that of the smaller mandrel. This can advantageously reduce the outer diameter of the inner coil by about 0.01".

Figure 5:
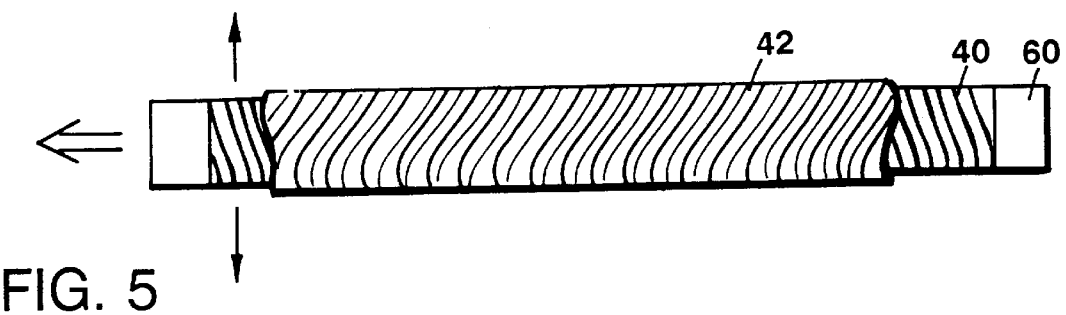
FIG. 5 is a longitudinal view of a partially constructed drive shaft.

Referring to FIG. 5, the inner coil 40 wound in conventional manner on the mandrel 60 is now small enough to be inserted in the outer coil 42 without interference. After the inner coil is inserted in the outer coil, the inner coil is released so that it springs toward its original diameter, causing it to engage the inner diameter of the outer coil with interfering contact. The mandrel is then removed and the two coils are secured at one end together by an adhesive, such as a high-temperature epoxy, or by a clamp, such as a copper or steel wire tightly wound around the clamped end.

After the coils are assembled, the inner coil is torqued in the opposite direction in which it was wound to expand it, while the outer coil is simultaneously torqued to reduce its diameter, causing the two coils to interfere more tightly. Since the coils are counterwound, the torque is applied in the same direction on each of the coils. This results in the bands of the multifilar elements being uniformly distributed.

Figure 6:
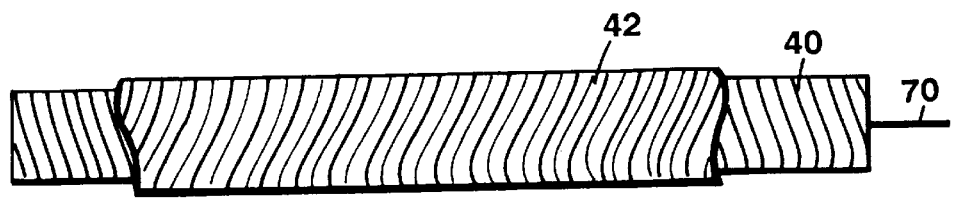
FIG. 6 is another longitudinal view of a partially constructed drive shaft.

In another embodiment, the inner coil 40 is released from a first mandrel and then, for assembly, attached to a "fishing" line 70, shown in FIG. 6. The inner diameter of the inner coil is reduced by applying tension to the line while pulling the inner coil through the outer coil 42.

Figure 7:
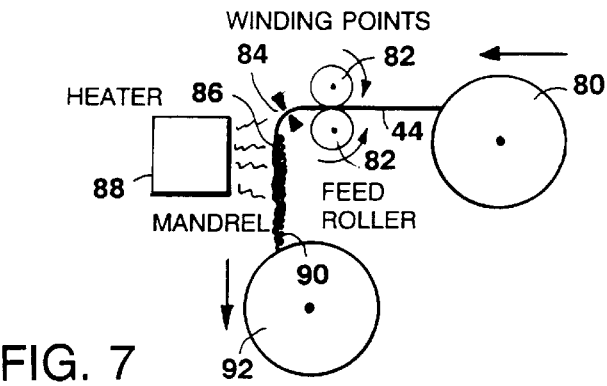
FIG. 7 is a schematic diagram of a nitinol coil under construction.

In another production method, shown in FIG. 7, a nitinol wire 44 is drawn from a supply roll 80 through feed rollers 82, and then passes through winding points 84, a pair of which bend the wire into a coil 86. The winding points are made of a very hard substance, such as steel, that is not subject to wear. A heating stage 88 heats the coil coming off the winding points, making wire 44 superelastic. The coil then slides onto a mandrel 90. After the superelastic coil unwinds off the mandrel, it springs back to its initial shape before being wound on a take-up reel 92.

Figure 8:
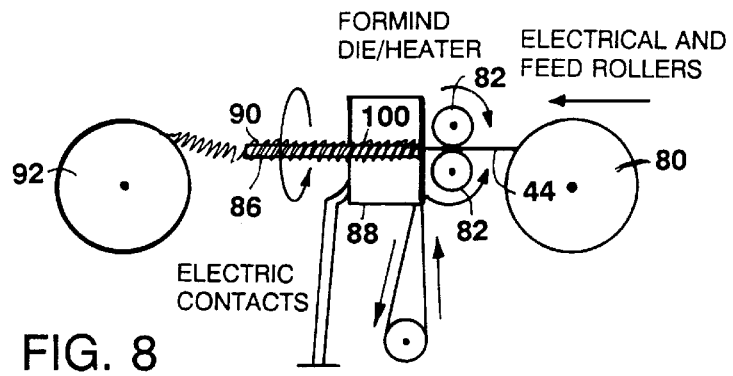
FIG. 8 is another schematic diagram of a nitinol coil under construction.

In another method of manufacture of the coil, shown in FIG. 8, a wire 44 winds off a supply roll 80 to feed rollers 82. The wire is then pulled onto a rotating die 100 in the form of a screw with a central mandrel. A forming heater 88 heats the wire wound onto the mandrel as the die rotates. Mandrel 90 holds wound coil 86 as it cools, and a take-up reel 92 takes up the coil as it winds off mandrel 90.

Figure 9:
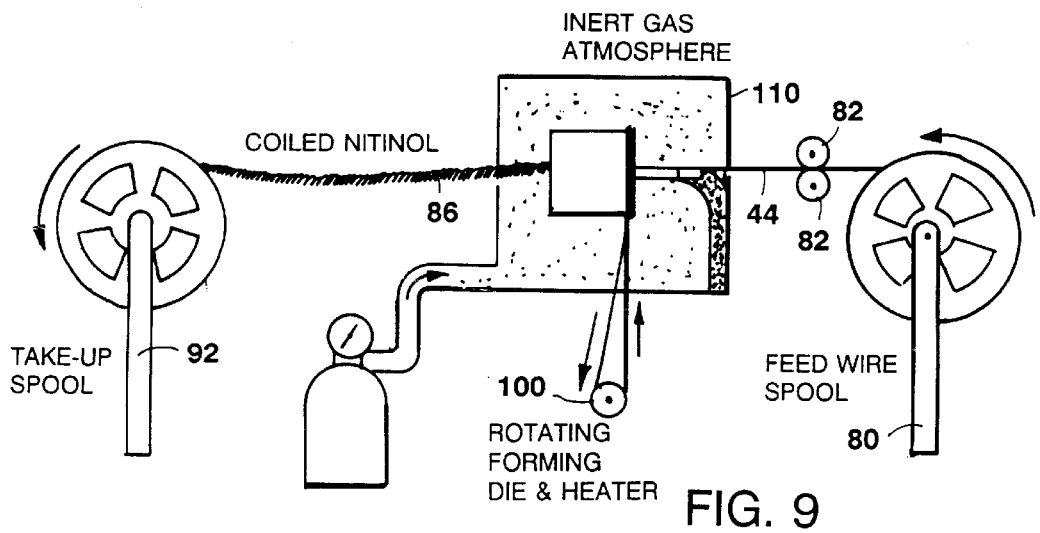
FIG. 9 is another schematic diagram of a nitinol coil under construction.

The rotating die is placed in an inert gas chamber 110, seen in FIG. 9, to help prevent contamination of the nitinol. Multiple spools 92 wind the multiple wires 44 with a winding machine that has a variable drive rate according the number of filaments being wound or the band width of the multifilar set of filaments. The number of spools used are from 3 to 8. The wires are led to a winding head, wrapped around a mandrel, and taped or mechanically secured. As the mandrel rotates, the wire is deformed under a wear resistant carbide shoe and wrapped around the mandrel. The carbide shoe maintains tension on the non-superelastic wire to produce tightness of the coils. When the coil on the mandrel is heated, the heat treating relaxes tension in the wire and the resulting superelastic coil is stress-neutral.

We have found that a drive shaft made from the superelastic coils is more resistant to mishandling damage, such as being twisted or bent during manufacture as well as when the catheter may be caught between medical devices in a lab or during insertion. Kinks are much less likely to form in the drive shaft, so that the resulting image will be free of drive shaft artifact.

Final assembly of the imaging catheter

Returning to FIG. 3, after the drive shaft is assembled, a very small (0.0055" to 0.009" outer diameter) electrical coaxial cable 120 is placed through its center. A transducer housing containing a transducer is attached to one end of the drive shaft with an epoxy. The transducer is connected to the coaxial cable 120, and the drive shaft is connected to an electrical connector. Such catheters are made in 6.0 French, 4.8 French, 3.5 French, and 3 French sizes.

For some applications, the preferred outer dimension of the catheter is 0.018" with a 0.013–0.014" outer diameter drive shaft if the catheter has a sheath. This is accomplished with 0.002" diameter round cross section wire, a 0.0055" outer diameter coaxial cable, and a 0.006" diameter mandrel. Other embodiments of the drive shaft In other embodiments, the drive shaft has a coil combined with a constraining element that opposes any change in size of the coil as it rotates. If the constraint is placed inside the coil, the coil is driven in the direction tending to reduce its diameter while the constraint resists contraction of the coil. If the constraint is outside the coil, the coil is driven in the direction tending to unwind the coil while the exterior constraint resists expansion of the coil. Such construction enables high fidelity, flexible drive shafts to be formed with the advantages of the present invention.

Figure 10:
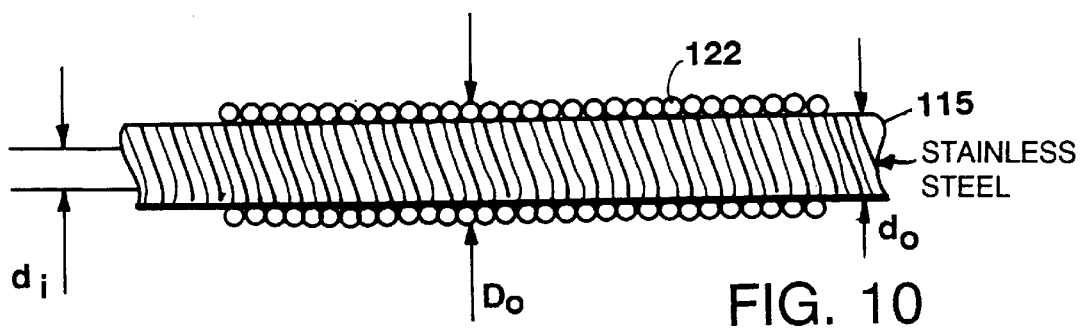
FIG. 10 is a cut-away view of a drive shaft in one embodiment.

In the embodiment shown in FIG. 10, the drive shaft has an inner coil 115 of stainless steel and an outer coil 122 of nitinol. The steel coil has an inner diameter $d_i$ of 0.008" and an outer diameter $d_o$ of 0.012"; the nitinol has an outer diameter $D_o$ of 0.016".

In this arrangement, the outer superelastic coil, which, due to geometrical considerations, is stressed more during bending than is the inner coil, is better able to resist yielding or kinking than a steel coil. The springback properties of the steel coil are used to easily achieve good distribution of the coils and an initial level of interference between the inner and outer coil, eliminating the need to wind the inner coil on a reduced size mandrel before insertion into the outer coil.

A structure with an inner superelastic coil and an outer stainless steel coil can provide good torsional performance while also providing adequate resistance to kinking under certain circumstances.

Figure 11:
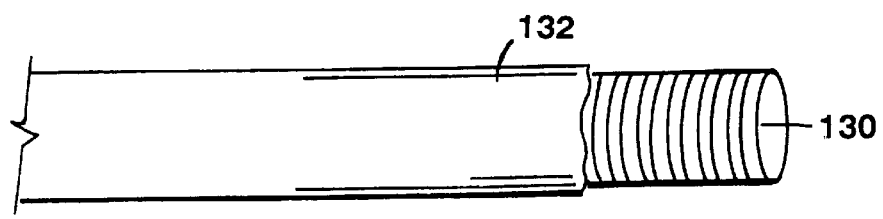
FIG. 11 is a side view of the drive shaft in another embodiment.

Referring now to FIG. 11, the drive shaft in another embodiment is composed of a single multifilar nitinol coil 130 and an outside sleeve 132 of a very thin (0.002") polyester material that constrains the coil. The polyester sleeve has the lateral support of the nitinol all along its length so that under axial columnar load it does not kink, i.e., it is not subject to columnar collapse.

Use of the thin polyester outer sleeve enables the total coil wall thickness of the drive shaft to be quite small. The imaging catheter using this type of drive shaft therefore can have an extremely small outer diameter and be capable of accessing very restricted regions of the body.

The nitinol coil and the polyester tube are constructed by winding the inner nitinol coil on a reduced size mandrel as mentioned above, fixing a tube around the coil and mandrel, and releasing tension on the coil so that it springs out against the tube. In another embodiment, the drive shaft is made by placing the inner coil on a mandrel, and then heat shrinking over that inner coil a heat shrinkable polyester tube.

Figure 12:
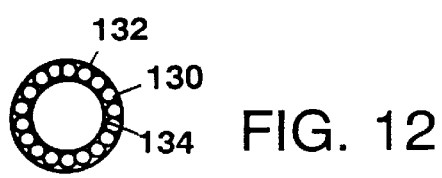
FIG. 12 is a cross-sectional view of the drive shaft in another embodiment.

In another embodiment, seen in FIG. 12, the nitinol coil 130 is embedded between two polyester coatings 132, 134. The layered construction has an inner coil that is a braided wire instead of a spring winding, that is wound over an existing length of extruded tubing. Polymer tubings are subsequently shrunk over the braided winding. The final wall thickness of the drive shaft is 3 to 4 layers thick.

In yet another embodiment, instead of using a preformed tube, the coil is run through an extruder that extrudes the polyester layer on the outside of the coil. The outer diameter of the coil and the gap between each winding of the coil is tightly controlled by winding the coil on a mandrel, allowing a very uniform coating of polymer to be placed on the coil to form a flexible drive shaft. Such a drive shaft can have applications in imaging catheters with an outer diameter of 0.018 inches or smaller.

Nitinol coils manufactured in the ways just described can thus be joined to or embedded in the walls of thin tubes, or coated to form such tubes, to enhance the compression resistance of thin walled tubular members over a wide range of tube diameters for use in catheters. The provision of such kink resistant catheter walls is another important feature of the present invention.

Figure 13:
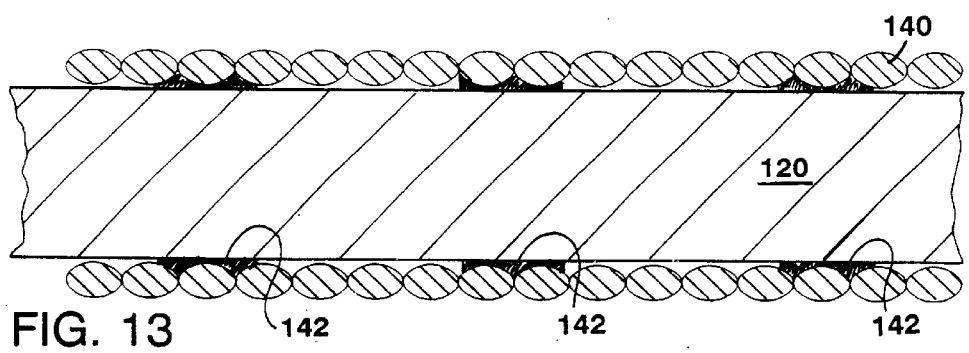
FIG. 13 is a cut-away view of a drive shaft.

Referring now to another embodiment of a drive shaft for acoustic imaging, shown in FIG. 13, a single nitinol coil 140 is bonded periodically to a coaxial cable 120 in its center to maintain stress on the coil. The coaxial cable is an electrical transmission line with 0.0055" to 0.010" outer diameter. The coaxial cable may also have an outer sheath that is plastic. If it is unsheathed, the coaxial cable has an inner conductor with an insulator that is very carefully controlled in thickness and an outer conductor (copper) which conforms to the insulator.

After the coaxial cable is threaded through the nitinol coil, an adhesive is applied to bind the coil to the coaxial cable along its entire length with half an inch to two inches spacing between successive bonds 142. The adhesive is a flexible epoxy in order to have a flexible drive shaft, and is low viscosity, so that it can penetrate easily between the windings of the coil. The coil is radially compressed during the bonding to reduce the space between the coaxial cable and the coil and to maintain the coil in a state of tension. Bonding the coil to the coaxial cable thus can limit the amount of wind up that may occur over the length of the coil, and thus can serve to reduce drive shaft artifact.

Using a single layer coil bonded to a coaxial cable or to polyester tubing is a preferred embodiment in certain instances when the wall thickness of the drive shaft needs to be limited to achieve a small outer diameter. The single layer coil construction reduces the outer diameter of the drive shaft by two wire diameters over an interfering dual coil construction. This enables the drive shaft to enter deeply into the body and into highly restricted regions, such as the coronary arteries and the neurovascular system. Larger coils, such as the dual coil drive shaft described above, are advantageous in imaging the gastrointestinal, urinary and esophageal tracts, the gall bladder, the peripheral arteries and other body ducts.

Other embodiments are within the following claims.

What is claimed is:

1. A method of forming a superelastic drive shaft comprising the steps of providing coils made of nickel-titanium alloy superelastic material, reducing the diameter of a first coil of superelastic material from its original diameter to a reduced diameter inserting the first coil while in a reduced diameter state into an inner lumen of a second coil of superelastic material, the second coil being wound in a direction opposite to the direction of winding of the first coil, and having an inner luminal diameter that is larger than an outside diameter of the first coil while in a reduced diameter state, and releasing the first coil from a reduced diameter state allowing it to spring toward its original diameter and interferingly engage the second coil.

2. The method of claim 1 further comprising the steps of
   torquing the first coil to expand its outer diameter, and
   torquing the second coil to reduce its inner diameter causing the first and second coils to interfere more tightly.

3. The method of claim 1 further comprising the steps of sliding said first coil onto a mandrel having a smaller diameter than an original inside diameter of said first coil, securing one end of said first coil to said mandrel, tightening said first coil until its inside diameter conforms to the mandrel, inserting the first coil while still conforming to the mandrel into the inner lumen of said second coil, and releasing the first coil from the mandrel allowing it to spring toward its original diameter and interferingly engage the second coil.

4. The method of claim 1 further comprising the steps of stretching said first coil to reduce its diameter.

5. A method of forming a coil of superelastic material for a catheter drive shaft comprising the steps of
   a) providing a first length of wire of latent superelastic properties from a wire supply of a nickel-titanium alloy,
   b) winding said first length of wire about a mandrel to form a coil,
   c) subjecting said first length of wire to heating conditions sufficient to stress relieve the first length of wire and convert it to having superelastic properties, and
   d) removing said first length of wire having superelastic properties from the mandrel,
   e) forming a first coil of superelastic material according to steps a through d wound in a first direction,
   f) separating said first coil from the wire supply,
   g) forming a second coil of superelastic material according to steps a through d wound in a second direction opposite said first direction,
   h) separating said second coil from the wire supply, and
   i) inserting said second coil within an inner lumen of said first coil.

6. The method of claim 5 wherein said winding is performed by a pair of winding points.

7. The method of claim 6 wherein said winding is performed by a rotating die.

8. The method of claim 7 wherein said heating and winding are performed while a said first length of wire is in an inert gas chamber.

9. The method of claim 5 wherein said first length of wire is subjected to heating conditions while said first length of wire is on the mandrel.

10. The method of claim 5 wherein said first length of wire is subjected to heating conditions prior to winding said first length of wire about the mandrel.

11. The method of claim 5 further including the step of cooling said first length of wire while said first length of wire is on the mandrel.

12. The method of claim 5, wherein the superelastic properties of said first length of wire include elastic deformation in the range of about three (3) to nine (9) percent.

13. The method of claim 5 wherein the superelastic properties of said first length of wire include recoverable deformation in the range of four (4) to seven (7) percent.

14. The method of claim 5, further comprising the step of subjecting said first length of wire to an annealing temperature of 450° C.

* * * * *